(12) United States Patent
Hansen et al.

(10) Patent No.: US 11,328,826 B2
(45) Date of Patent: May 10, 2022

(54) SYSTEM ARCHITECTURE FOR IMPROVED STORAGE OF ELECTRONIC HEALTH INFORMATION, AND RELATED METHODS

(71) Applicant: Clarius Mobile Health Corp., Burnaby (CA)

(72) Inventors: Trevor Stephen Hansen, North Vancouver (CA); Benjamin Eric Kerby, Richmond (CA); Dongkang Li, New Westminster (CA); Shirui Yin, Burnaby (CA)

(73) Assignee: Clarius Mobile Health Corp., Vancouver (CA)

( * ) Notice: Subject to any disclaimer, the term of this patent is extended or adjusted under 35 U.S.C. 154(b) by 0 days.

(21) Appl. No.: 16/006,230

(22) Filed: Jun. 12, 2018

(65) Prior Publication Data

US 2019/0378623 A1    Dec. 12, 2019

(51) Int. Cl.
| | | |
|---|---|---|
| *G16H 80/00* | (2018.01) | |
| *G16H 10/60* | (2018.01) | |
| *H04L 67/306* | (2022.01) | |
| *H04L 67/1097* | (2022.01) | |
| *G06F 16/29* | (2019.01) | |

(52) U.S. Cl.
CPC ............ *G16H 80/00* (2018.01); *G06F 16/29* (2019.01); *G16H 10/60* (2018.01); *H04L 67/1097* (2013.01); *H04L 67/306* (2013.01)

(58) Field of Classification Search
CPC .............. H04L 61/1511; H04L 61/609; H04L 67/2814; H04L 67/02; H04L 61/6009; H04L 63/0281; H04L 67/306; H04L 61/2007; H04L 67/2842; H04L 63/10; H04L 63/08; H04L 47/20; H04L 41/28; H04L 67/32; H04L 47/80; H04L 47/803; H04L 67/10; H04L 67/42; H04L 63/04; H04L 63/0428; H04L 67/1097; H04L 67/18; H04L 63/107; H04W 12/06; G16H 10/60; G16H 80/00; G16H 40/20; G16H 70/20; G06Q 30/0205; G06F 21/6245; G06F 16/122

See application file for complete search history.

(56) References Cited

U.S. PATENT DOCUMENTS 7,406,071 B1 * 7/2008 Tang ....................... H04L 61/00
                                                                    370/254
8,589,355 B2   11/2013 Nagpal et al.
(Continued)

*Primary Examiner* — Tonia L Dollinger
*Assistant Examiner* — Linh T. Nguyen
(74) *Attorney, Agent, or Firm* — Julian Ho

(57) ABSTRACT

The present embodiments relate generally to a system for improved storage of electronic health information, the system including: a computing device for receiving the electronic health information; and a server for communicating with the computing device, the server being accessible by the computing device at a first network location. The server can be configured to: receive a request from the computing device for a second network location, the second network location usable for storing the electronic health information, and the second network location being different from the first network location; determine the second network location; and provide the second network location to the computing device; and the computing device stores the electronic health information at the second network location.

14 Claims, 8 Drawing Sheets

(56) References Cited

U.S. PATENT DOCUMENTS

| | | | |
|---|---|---|---|
| 8,676,593 B2 | 3/2014 | Nagpal et al. | |
| 10,192,229 B2* | 1/2019 | Ghosh | G06F 16/29 |
| 2005/0021376 A1* | 1/2005 | Zaleski | G16H 40/67 |
| | | | 705/3 |
| 2006/0241977 A1* | 10/2006 | Fitzgerald | G16H 20/00 |
| | | | 705/3 |
| 2007/0271316 A1* | 11/2007 | Hollebeek | G06F 11/1464 |
| 2008/0004818 A1* | 1/2008 | Zaleski | A61M 1/777 |
| | | | 702/50 |
| 2011/0314082 A1* | 12/2011 | Koneti | G06F 9/5055 |
| | | | 709/203 |
| 2013/0036100 A1 | 2/2013 | Nagpal et al. | |
| 2013/0067530 A1* | 3/2013 | Spektor | H04L 61/305 |
| | | | 726/1 |
| 2013/0215277 A1* | 8/2013 | Kang | H04N 5/30 |
| | | | 384/163 |
| 2013/0332723 A1* | 12/2013 | Tan | H04L 63/0807 |
| | | | 713/150 |
| 2014/0201218 A1 | 7/2014 | Catalano et al. | |
| 2014/0207818 A1* | 7/2014 | Jellick | H04L 41/082 |
| | | | 707/771 |
| 2015/0381571 A1* | 12/2015 | Plasse | H04L 51/00 |
| | | | 726/26 |
| 2016/0099924 A1* | 4/2016 | Mehta | H04L 61/1576 |
| | | | 726/7 |
| 2016/0191455 A1* | 6/2016 | Newton | G06F 16/48 |
| | | | 709/245 |
| 2016/0205035 A1* | 7/2016 | Kurian | H04L 47/783 |
| | | | 726/4 |
| 2016/0234265 A1* | 8/2016 | Lohe | H04L 65/403 |
| 2017/0208048 A1* | 7/2017 | Broussard | H04L 63/0428 |
| 2017/0308647 A1* | 10/2017 | Reicher | G16H 40/20 |
| 2017/0325286 A1* | 11/2017 | Le | H04L 12/4641 |
| 2018/0053012 A1* | 2/2018 | Myers | G06F 16/972 |
| 2018/0241569 A1* | 8/2018 | Harmon | H04L 63/107 |
| 2019/0046035 A1* | 2/2019 | Nyquist | H04L 67/1085 |
| | | | 709/217 |
| 2019/0108919 A1* | 4/2019 | Shim | G16H 30/20 |

* cited by examiner

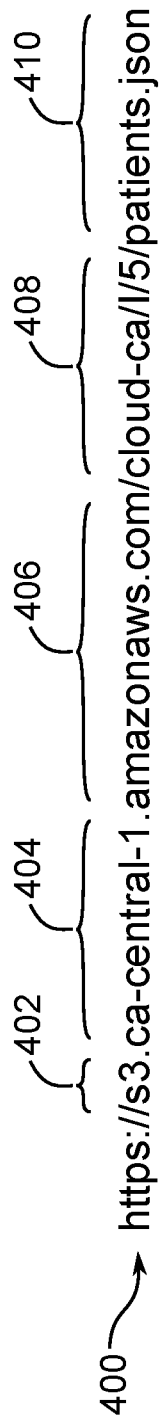

```
{
    "00829c01e49f412345f6eed17e596666": {
        "date_of_birth": "1988-01-18",
        "first_name": "John",
        "gender": "M",
        "identifier": "1281810839",
        "identifier_display": "1281810839",
        "institution_id": 5,
        "last_modified": "2018-03-02T01:42:30.781372+00:00",
        "last_name": "Doe",
        "middle_name": "Bradley",
        "uuid": "00829c01e49f412345f6eed17e596666"
    },
    "00f3f19a25054257a12345e30dc8e6f7": {
        "date_of_birth": "1990-04-28",
        "first_name": "Jane",
        "gender": "F",
        "identifier": "1281810840",
        "identifier_display": "1281810840",
        "institution_id": 5,
        "last_modified": "2018-03-02T01:42:29.715225+00:00",
        "last_name": "Doe",
        "middle_name": "Mary",
        "uuid": "00f3f19a25054257a12345e30dc8e6f7"
    },
    "011fbbc77fd12345a1936bea123e45d9": {
        "date_of_birth": "1976-06-30",
        "first_name": "Jamie",
        "gender": "X",
        "identifier": "1281810841",
        "identifier_display": "1281810841",
        "institution_id": 5,
        "last_modified": "2018-03-09T01:48:42.771600",
        "last_name": "Goldberg",
        "middle_name": "Brook",
        "uuid": "011fbbc77fd12345a1936bea123e45d9"
    }
}
```

SYSTEM ARCHITECTURE FOR IMPROVED STORAGE OF ELECTRONIC HEALTH INFORMATION, AND RELATED METHODS

FIELD

The present disclosure relates generally to online storage of electronic health information, and in particular, a system architecture for improved storage of electronic health information and related methods.

BACKGROUND

Cloud computing is a paradigm in which software tasks are assigned to a combination of connections, software and services that are accessed over a network. This network of servers and connections is collectively known as "the cloud." Different types of cloud services may be used in cloud computing. For example, cloud services may include access to computing resources of a server, and; or non-volatile storage of data. By using cloud computing resources, organizations needing computing resources may be able to access them without purchasing their own server computers.

Cloud computing have begun to be used in many industries. However, there has been resistance to cloud computing in the healthcare field because of heightened regulations governing storage and access of electronic health information such as patient records. For example, in the United States, the Health Insurance Portability and Accountability Act of 1996 (HIPA) requires additional technical safeguards when processing and storing electronic health information. As technical capabilities of cloud computing resources increased, adoption of cloud computing in the healthcare, field also increased. However, certain regulatory requirements still presented unique challenges.

Specifically, some jurisdictions have regulations that require electronic health information to be stored on servers that are physically located within that given jurisdiction. These "data residency" requirements often make it difficult for organizations to provide technical solutions that store electronic health information for patients from multiple jurisdictions. This is because cloud computing resources are traditionally provided in a localized manner, such that processing and storage resources are provided together physically in selectable geographic regions. Such a configuration allows for minimal latency when data is read and stored from cloud computing resources.

One potential solution to achieve compliance with data residency requirements is to replicate instances of the cloud computing and storage resources in every jurisdiction where patient data may be processed. However, such a solution may create difficulties for administration and maintenance because information and data (e.g., configuration settings) may also need to be replicated in every jurisdiction. This creates risks of incorrect/inconsistent data being deployed in multiple jurisdictions. Further, replicating instances of cloud computing and storage resources in every jurisdiction may involve increased costs.

There is thus a need for a system architecture for improved storage of electronic health information, and related methods. The embodiments discussed herein may address and/or ameliorate at least some of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF THE DRAWINGS

Non-limiting examples of various embodiments of the present disclosure will next be described in relation to the drawings, in which:

FIGS. 4 and 5 are example Uniform Resource Locators (URL) for accessing electronic health information, in accordance with at least one embodiment of the present invention;

FIG. 6 is an example of a file storing patient electronic health information, in accordance with at least one embodiment of the present invention;

DETAILED DESCRIPTION

Figure 1:
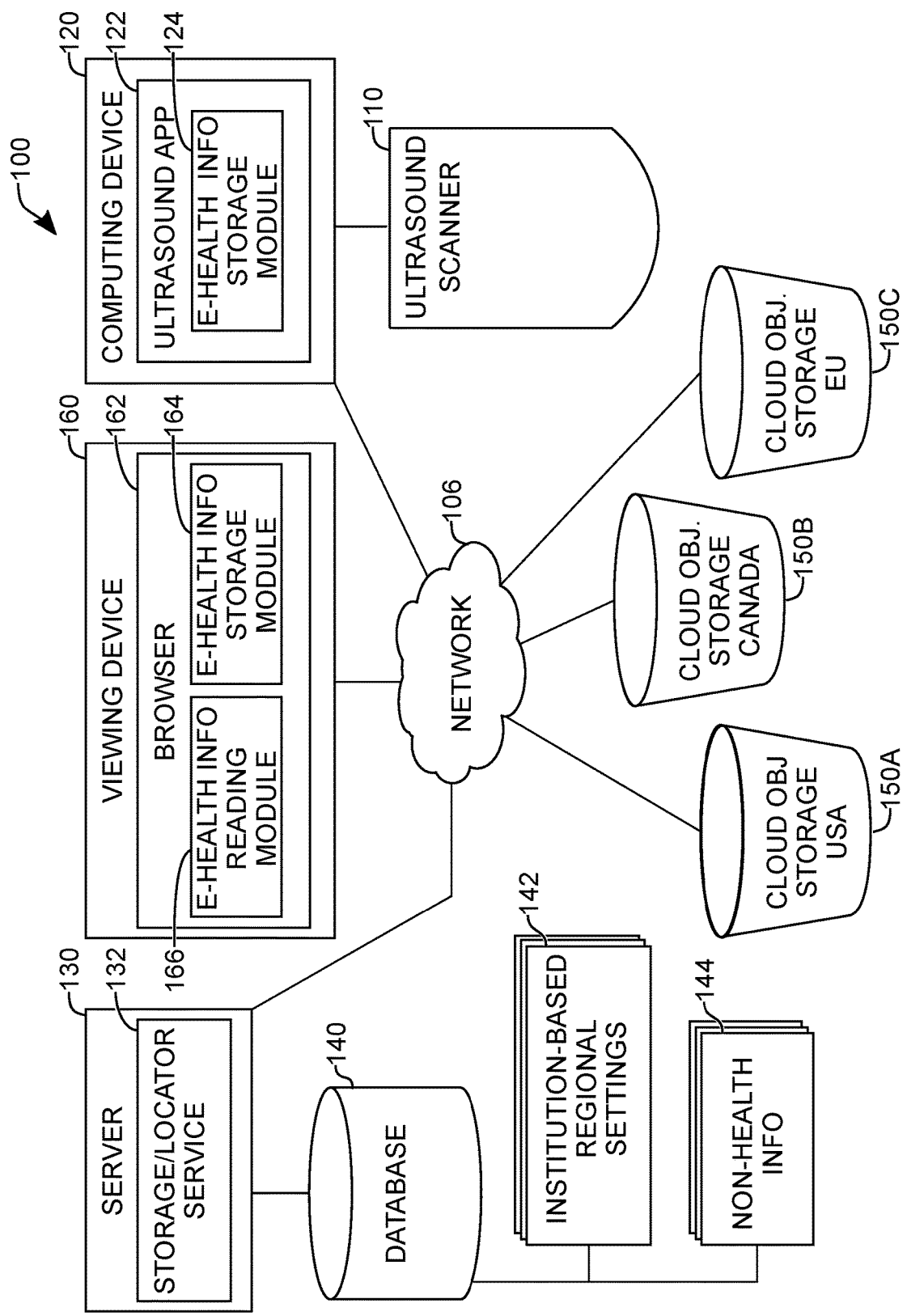
FIG. 1 shows a block diagram of a system for improved storage of electronic health information, in accordance with at least one embodiment of the present invention.

In a first broad aspect of the present disclosure, there is provided a system for improved storage of electronic health information, the system including: a computing device for receiving the electronic health information; and a server for communicating with the computing device, the server being accessible by the computing device at a first network location. The server can be configured to: receive a request from the computing device for a second network location, the second network location usable for storing the electronic health information, and the second network location being different from the first network location; determine the second network location; and provide the second network location to the computing device; wherein the computing device stores the electronic health information at the second network location.

In some embodiments, when determining the second network location, the server is further configured to: look up a geographical region storage setting associated with the computing device, and select the second network location based on the geographical region storage setting.

In some embodiments, the geographical region storage setting is associated with an institution profile of a logged-in user at the computing device.

In some embodiments, the server provides different network locations for different geographical region storage settings, and the server is further configured to store non-health information centrally at a single network location.

In some embodiments, the server is further configured to store an identifier of the electronic health information, and the identifier is usable by the server to read the electronic health information from the second network location.

In some embodiments, the server is further configured to provide a location service that, when accessed, returns a network location address corresponding to the second network location provided to the computing device, the network location address being usable by the server to read the electronic health information.

In some embodiments, the request to receive the second network location is transmitted by an application executing in the foreground of the computing device, and when the computing device stores the health information at the second network location, the computing device executes a background process to upload the electronic health information.

In some embodiments, the second network location for storing the electronic health information resolves to a data storage service accessible by the computing device via a Uniform Resource Identifier (URI).

In some embodiments, the data storage service stores unstructured data. In some embodiments, the server executes at least one process at the first network location, the server accesses a database at the first network location.

In some embodiments, the second network location for storing the electronic health information resolves to a remote database.

In some embodiments, the electronic health information includes one of: patient-identifying information and ultrasound media.

In another broad aspect of the present disclosure, there is provided a method for improved storage of electronic health information, the method performed by a server accessible by a computing device at a first network location, the method including: receiving a request from the computing device configured to receive the electronic health information, the request being for a second network location usable by the computing device to store the electronic health information, and the second network location being different from the first network location; determining the second network location; and providing the second network location to the computing device, wherein the computing device stores the electronic health information at the second network location.

In some embodiments, when determining the second network location, the method further includes: looking up a geographical region storage setting associated with the computing device, and selecting the second network location based on the geographical region storage setting.

In some embodiments, the geographical region storage setting is associated with an institution profile of a logged-in user at the computing device.

In some embodiments, the method further includes: providing different network locations for different geographical region storage settings, and storing non-health information centrally at a single network location.

In some embodiments, the method further includes: storing an identifier of the electronic health information, and the identifier is usable by the server to read the electronic health information from the second network location.

In some embodiments, the method further includes: providing a location service that, when accessed, returns a network location address corresponding to the second network location provided to the computing device, the network location address being usable by the server to read the electronic health information.

In another broad aspect of the present disclosure, there is provided a method for improved storage of electronic health information, the method performed by a computing device, the method including: transmitting a request to a server at a first network location, the request for retrieving a second network location usable by the computing device to store the electronic health information, and the second network location being different from the first network location, wherein the server: determines the second network location, and provides the second network location to the computing device; receiving the second network location from the server; and storing the electronic health information at the second network location.

In some embodiments, the request to receive the second network location is transmitted by an application executing in the foreground of the computing device, and when the computing device stores the health information at the second network location, the method further includes: executing a background process to upload the electronic health information.

In some embodiments, the second network location for storing the electronic health information resolves to a data storage service accessible by the computing device via a Uniform Resource Identifier (URI), and the storing of the electronic health information at the second network location is performed via the URI.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

Referring to FIG. 1, shown there generally as 100 is a block diagram of a system for improved storage of electronic health information, in accordance with at least one embodiment of the present invention. The system 100 may include an ultrasound scanner 110 communicably coupled with a computing device 120, a server 130, a database 140, and number of regional cloud object storage resources 150A, 150B, 150C (referred to herein generally as 150), and viewing device 160. In various embodiments, the cloud object storage resources 150 may also generally be referred to as "buckets". The computing device 120, server 130, cloud object storage resources 150, and viewing device 160 may be connected via a computer network such as the Internet.

The ultrasound scanner 110 may be configured to transmit ultrasound energy to a target object, receive ultrasound energy reflected from the target object, and generate ultrasound image data based on the reflected ultrasound energy. The ultrasound scanner 110 may include a transducer which converts electric current into ultrasound energy and vice versa. The transducer may transmit ultrasound energy to the target object which echoes off the tissue. The echoes may be detected by a sensor in transducer and relayed through suitable electronics that interpret and process the echoes to generate image data of the scanned tissue. In some embodiments, the ultrasound scanner 110 may be provided as a handheld ultrasound probe that transmits the image data to the computing device 120 for display thereon.

Ultrasound scanner 110 may include various components (not shown) for storing software or firmware instructions, configuration settings (e.g., sequence tables), and/or ultrasound image data. The ultrasound scanner 110 may also include one or more processors (not shown) for executing the instructions for performing acts of the methods discussed herein.

Computing device 120 may be a multi-use electronic display device such as a smartphone, tablet computer, or other suitable display device. In various embodiments, the computing device 120 may be provided with an input component capable of receiving user input (e.g., the input may contain electronic health information).

In the illustrated embodiment, certain input received at the computing device 120 may be relayed to ultrasound scanner 110 to control the operation of ultrasound scanner 110. Computing device 120 may also include an output component, such as a display screen, which displays images based on image data acquired by ultrasound scanner 110. For example, the computing device 120's input component may include a touch interface layered on top of the display screen of the output component. Electronic computing device 120 may also include memory, Random Access Memory (RAM), Read Only Memory (ROM), and persistent storage device, which may all be connected to a bus to allow for communication therebetween and with one or more processors. Any number of these memory elements may store software and/or firmware that may be accessed and executed by the one or more processors to perform the methods and/or provide the user interfaces described herein as being performed by or provided on the computing device 120.

In various embodiments, the computing device 120 may execute an application that is configured to communicate with the ultrasound scanner 110. In FIG. 1, this is shown as scanner application or "Ultrasound App" 122. This application 122 may also be generally referred to as the "Scanner App" herein. For example, in embodiments where the multi-use electronic computing device 120 provides a native software distribution platform (e.g., such as the Apple™ App Store™ for iOS™ devices or the Google™ Play Store™ for Android™ devices), the ultrasound app 122 may be downloaded therefrom. In an example embodiment, the scanner application 122 may be provided with an electronic health (e-health) information storage module 124 configured to store electronic health information received as input at the computing device 120. For example, the e-health information storage module 124 may be configured to perform various acts of the methods described herein as being performed by the computing device 120. The e-health information storage module 124 may also generally be referred to as the e-health storage module 124 herein.

While an ultrasound scanner 110 is shown in the example embodiment of FIG. 1, it may be omitted in some embodiments. For example, in some embodiments, the e-health information storage module 124 may be provided in a general e-health information input application executed on a computing device 120 that is unrelated to operation of ultrasound equipment.

Server 130 may be configured to provide a storage/locator service 132 (also referred to generally herein as a location service) to perform various acts of the methods discussed herein as being performed by the server 130. The server 130 may be accessible at a first network location (e.g., at a URL or at a given Internet Protocol (IP) address). In various embodiments, the storage/locator service 132 may be provided in the form of software instructions configured to execute on server 130. For example, the software instructions may provide an Application Programming Interface (API) that the e-health information storage module 124 on the scanner app 122 and/or the e-health information storage module 164 and/or the e-health information reading module 166 on the viewing device 160 is configured to access (as discussed below).

The server 130 may store information in a database 140. The database 140 may be a relational database, object-oriented database, or any other suitable type of database. As discussed below, non-health electronic information 144 may generally be stored in the database 140. However, e-health information may be stored in different cloud object storage resources 150. Notably, the server 130 and database 140 may generally be provided in the same geographical region, and accessible at the same network address. However, the different cloud object storage resources 150 may be accessible at network locations that are different from the network location for accessing the server 130 and/or database 140. In various embodiments, the storage/locator service 132 at the server 130 and the database 140 may be provided by one or more online cloud computing service providers. For example, the server 130 may be provided using Amazon™ Elastic Compute Cloud (Amazon EC2) and/or Google™ Compute Engine™. The database may be provided, for example, by Amazon™ Relational Database Service (RDS) and/or Google™ Cloud SQL™.

Non-health electronic information 144 may not be geographically restricted in the manner that e-health information is. For example, non-health electronic information 144 may include metadata associated with an examination that does not identify a specific patient (e.g., information about the medical professional performing the ultrasound scan); and/or statistics, log information, or the like about the usage of the ultrasound scanner 110. Additional examples of non-health information may include public information such as an institution name or other information about an institution such as its location, or the like.

When the storage/locator service 132 is accessed, it may return a second network location address different from the first network location address at which the server 130 is accessed. The requesting device (e.g., either computing device 120 and/or viewing device 160) may then use this second network address to read and/or store e-health information from/to a cloud object storage resource 150 identified by the second network address.

In various embodiments, electronic health information may be information that allows a patient to be identified. For example, in some embodiments, the electronic health information referred to herein may coincide with the defined meaning of Protected Health Information (PHI) under applicable U.S. regulations such as HIPAA. For example, this may include any information about health status, provision of health care, and/or payment of health care that can be linked to a specific individual. In various embodiments, electronic health information may include one or more of the following: names, geographical identifiers, dates, phone numbers, fax numbers, email addressed, social security numbers, and/or medical record numbers.

In various embodiments, the electronic health information may include one of: patient-identifying information and ultrasound images. As noted, the patient-identifying information may be entered on the ultrasound app 122 when it is generating images in connection with the ultrasound scanner 110.

The specific cloud object storage resource 150 that any given e-health information is stored in may be selected based on a geographical region setting. For example, the server 130 may provide different network locations for different geographical region storage settings. During operation, a computing device 120 may access the server 130 at a first network location to communicate with the storage/locator service 132. The storage/locator service 132 may be configured to provide to the computing device 120 the second network location of the cloud object storage resource 150 that is suitable for the requesting computing device 120 based on the geographical region setting. As discussed in greater detail in relation to FIG. 2, geographic region settings may be associated with an institution profile associated with a user. For example, in FIG. 1, the regional settings are shown as institution-based regional settings 142 stored in database 140.

As compared to the storage of electronic health information in regional cloud object storage resources 150, the server 130 may be configured to store non-health information 144 centrally at a single network location. For example, the server 130 may store non-health information at the database 140 which is at the same network location as the server 130. As compared to other system architectures for facilitating compliance with data residency requirements that instantiate servers 130 and databases 140 in every geographical region where storage is desired, the present embodiments can reduce the complexity and cost from such duplicated instantiations. At the same time, compliance with data residency regulations governing storage of electronic health information can still be achieved.

As discussed below, the network location of the cloud object storage resources 150 may resolve to online storage resources that do not need corresponding online computer processing resources to be instantiated. For example, these online storage resources 150 may be simple object storage resources that are simpler to access and instantiate than a cloud relational database service. Such simple online object storage resources 150 may be accessible via a URL. Examples of cloud object storage resources 150 include Amazon™ Simple Cloud Storage Service (S3) and Google™ Cloud Storage™. Notwithstanding, in some embodiments, it may also be possible for the electronic health information to be stored in remote databases instantiated in each desired geographic region. For example, in such embodiments, the second network location returned by the storage/locator service 132 may resolve to a remote database. As discussed in greater detail below, use of cloud object storage resources 150 for storage (as opposed to remote databases) may also allow for uploading of electronic health information using a background process on certain operating systems of computing device 120.

The viewing device 160 can be any suitable computing device used to communicate with the server 130 and/or one or more cloud object storage resources 150 to retrieve and/or store electronic health information and non-health information. For example, the viewing device 160 may be a desktop computer with a web browser 162 that is configured to execute client-side programming instructions such as JavaScript™ to provide a display of exams obtained via use of a computing device 120 with the ultrasound scanner 110 to perform medical examinations. For example, the exams may include ultrasound images and/or cineloops, and be associated with electronic health information such as patient identifiers.

The browser 162 may be configured to execute an e-health information storage module 164 that stores e-health information. The e-health information storage module 164 may accesses the storage/locator service 132 to store e-health information into the cloud object storage resources 150. For example, the storage/locator service 132 may provide the viewing device 160 with a URL to access the appropriate cloud object storage resource 150, so that the viewing device 160 stores the e-health information into a cloud object storage resource 150 directly. Additionally or alternatively, the e-health storage module 164 may provide the e-health information to the storage/locator service 132 and such service 132 may store the information into the appropriate the cloud object storage service 150.

The browser 162 may also be configured to execute an e-health information reading module 166 that reads e-health information. This may generally be referred to as the e-health reading module herein. For example, the e-health reading module 166 may similarly access the storage/locator service 132 to read e-health information. For example, the storage/locator service 132 may provide the viewing device 160 with a URL to access the appropriate cloud storage resource 150, so that the viewing device 160 reads the e-health information from the cloud object storage resource 150 directly. Additionally or alternatively, the storage/locator service 132 may look up the appropriate cloud object storage resource 150 and read the e-health information directly from the appropriate cloud object storage service 150. The storage/locator service 132 may then return the e-health information to the e-health reading module 166.

As will be understood by persons skilled in the art, the architecture in FIG. 1 is provided for illustration only. Other configurations may be possible in other embodiments.

Figure 2:
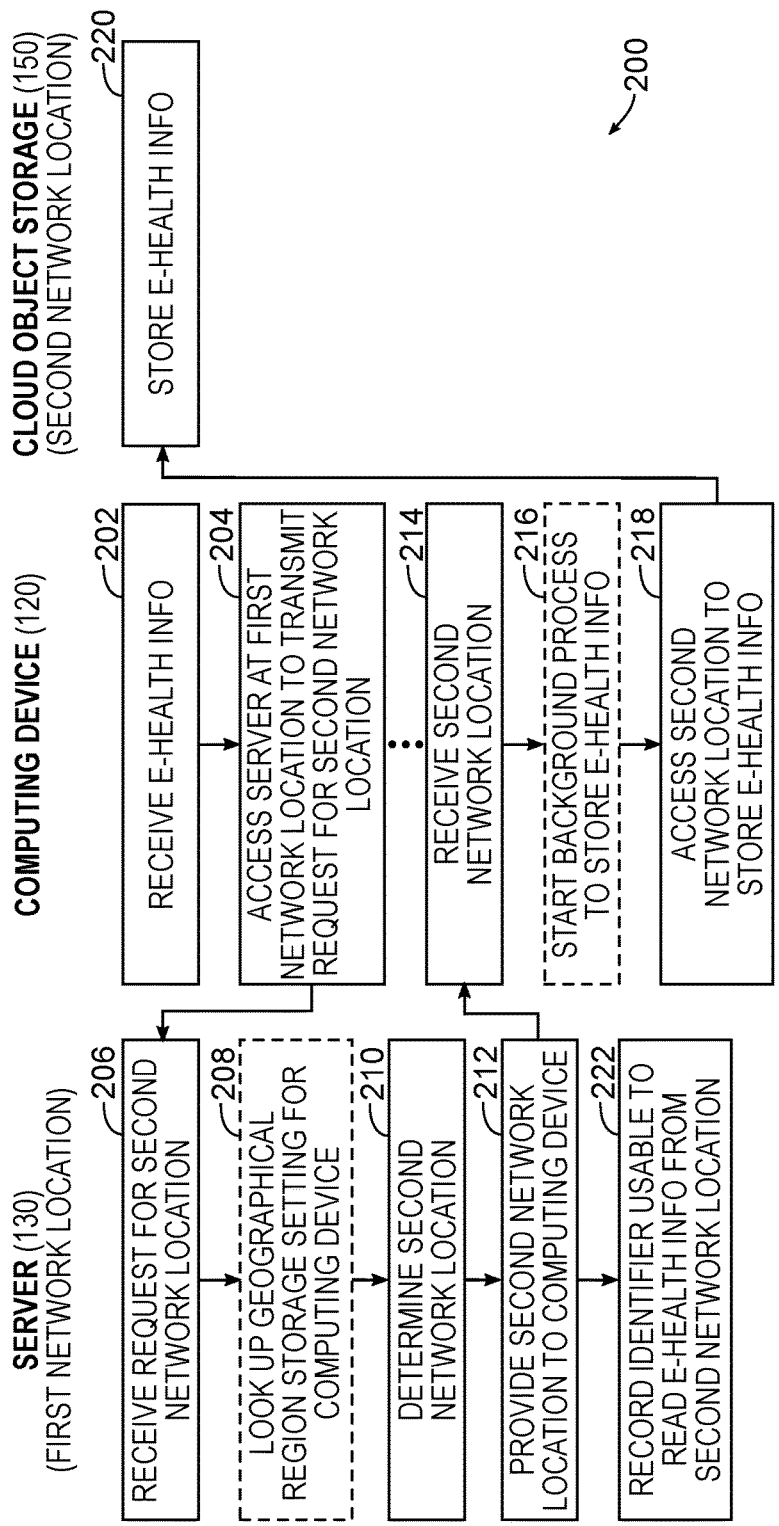
FIG. 2 is a flowchart diagram showing acts for storing electronic health information, in accordance with at least one embodiment of the present invention.

Referring to FIG. 2, shown there generally as 200 is a flowchart diagram showing acts for storage of electronic health information, in accordance with at least one embodiment of the present invention. In discussing the acts of FIG. 2, reference will also be made to various elements shown in FIG. 1. Method 200 generally illustrates interactions amongst the server 130, the computing device 120, and a cloud object storage service 150 shown in FIG. 1. In FIG. 2, various acts shown as being performed by the server 130 may be performed by the storage/locator service 132, and various acts shown as being performed by the computing device 120 may be performed by the ultrasound application 122 and/or more specifically, the e-health information storage module 124. In discussing the method 200, reference may also be made to the URLs shown in FIGS. 4 and 5, as well as the patient-identifying information file shown in FIG. 6.

At 202, the computing device 120 may receive electronic health information. For example, when a computing device 120 is being used with ultrasound scanner 110, the ultrasound app 122 may be configured to acquire ultrasound media (e.g., images and/or cineloops) of internal anatomy of a patient. The ultrasound app 122 may be able to organize acquired ultrasound media as an examination for a given patient, such that the ultrasound app 122 may present suitable user interface screens that allow for input of information related to the patient (e.g., patient names, birthdate, gender, institution, and/or other suitable patient identifiers).

In various embodiments, the determination of whether certain information received at the computing device 120 is electronic health information or non-health information (e.g., that may or may not need to be geographically segregated) may be pre-classified. For example, such pre-classification may be based on fields identified during creation of the ultrasound app 122. In various embodiments, pre-classification may be based on regulatory requirements (e.g., HIPAA) for which fields constitute patient identifiers. Additionally or alternatively, the classification of information into health and non-health information may be performed dynamically based on an information classification setting available on server 130.

In various embodiments, generated ultrasound media and any entered electronic health information may be temporarily stored on the computing device 120 until the subsequent acts discussed herein to upload such information onto cloud computing resources are performed. In various embodiments, such data may be encrypted (e.g., if storage encryption is part of the native operating system and/or if storage encryption is based on a setting, such setting is enabled).

At 204, the computing device 120 may access the server 130 at a first network location, to transmit a request for retrieving a second network location usable by the computing device 120 to store the electronic health information. For example, the server 130 may be provided at a geographical location that may not be suitable for storing the electronic health information from the computing device 120. As noted, to allow for compliance with certain regulatory requirements, it may be desirable to store the electronic health information within certain geographical locations. The request at 204 may be to obtain the second network location (different from the first network location) where the electronic health information is to be stored. At act 206, this request may be received at the server 130 (e.g., by the storage/locator service 132). In various embodiments, the communications between the computing device 120 and the server 130 described herein may be encrypted (e.g., using 128-bit Transport Layer Security (TLS) 1.2 encryption or higher). In various embodiments, act 204 may be executed as a foreground process at the computing device 120.

At act 208, the server 130 may look up a geographical region storage setting associated with the computing device 120 making the request at act 204, and select the second network location based on the geographical region storage setting. In some embodiments, the ultrasound app 122 executing on computing device 120. A given user account may be associated with a geographical region setting, such that the server 130 may determine the geographical region setting to return to the computing device 120 based on the user account that is logged-in at the computing device 120.

Additionally or alternatively, a user account may be associated with an institution profile that has a geographical region setting for all users associated with such institution profile. In this scenario, the geographical region setting determined by the server 130 may be associated with an institution profile of a logged-in user at the computing device 120. For example, by virtue of a given user account being logged into the scanner app 122, the computing device 120 may be considered as being associated with the institution profile of the user account. In this example embodiment, the scanner app 122 may thus also have access to an institution account identifier of the logged-in user account.

As used herein, the term "institution" may refer to a hospital, clinic, medical practice, or any other collection of one or more users. In some embodiments, an "institution" may have a single user. In some embodiments, institutions may be provided in a tiered or nested fashion. For example, an institution may have internal departments, divisions, or the like; and a user account may additionally or alternatively be associated with one or more such departments or divisions within an institution. In embodiments with an ultrasound scanner 110, the ultrasound scanner 110 may also be associated with an institution.

Act 208 is one example way of the server 130 determining the second network location for a computing device 120. However, there may be other ways in which the server 130 determines the second network location. Act 208 is thus optional (shown in dotted outline) and may not be performed in all embodiments. For example, in some embodiments, the second network location to be returned to the computing device 120 may be determined based on Global Positioning System (GPS) or other geolocation information (e.g., an IP address or other domain name, and/or the jurisdiction of the native software distribution platform (e.g., the App Store™) on the operating system) of the computing device 120. Additional or alternative geolocation determination mechanisms that may also be used include: determined based on Wi-Fi™ signals, and/or other conventionally known or later developed means for determining the geographical location of the computing device 120.

For example, such geography identifying determinations may indicate that the computing device 120 is physically located in the United States. This information (e.g., GPS coordinates) may be included in the request sent from the computing device 120 to the server 130. The server 130 may then, using this information, determine the second network location of the cloud object storage resource 150A for storing electronic health information from the United States.

As a result of the geographical region storage setting and/or geolocation information of the computing device 120, the second network location may be determined at server 130 (act 210). At 212, the server 130 may provide the second network location to the computing device 120. At 214, the computing device 120 may receive the second network location from the server 130. For example, if the geographical region storage setting and/or the geolocation information indicates the cloud object storage resource for the United States 150A is to be used, the server 130 may provide the second network location for that cloud object storage resource 150A back to the computing device 120.

The second network location may be provided to the computing device 120 in various ways. For example, the second network location may be provided in the form of an IP address and port number. Additionally or alternatively, the second network location may be provided in the form of a Uniform Resource Identifier (URI), that resolves to a data storage service accessible by the computing device 120. Any type of URI may be used with the embodiments described herein. However, for illustrative purposes, the embodiments described herein generally relate to Uniform Resource Locators (URLs).

Referring to FIG. 4, shown there generally as 400 is an example URL for accessing electronic health information, in accordance with at least one embodiment of the present invention. For example, a URL formatted in this way may be provided by the server 130 to the computing device 120 at act 212. In FIG. 4, an example URL for accessing electronic health information on a cloud object storage resource 150 is shown.

As illustrated, the URL 400 has multiple components that allow it to resolve to the appropriate web service. The example URL is provided by Amazon™ Web Services (AWS); however, analogous principles may be used with other cloud service providers. As shown, the component 402 indicates the service being accessed. Specifically, as noted above, the text 'S3' refers to Amazon's Simple Cloud Storage Service.

Next, the component 404 refers to the geographic region that is the entry point for the web service being accessed. As shown, the region being accessed is 'ca-central-1', referring to the 'Canada (Central)' region provided by AWS. Component 406 refers to the domain name for accessing the cloud service provider's cloud computing and/or storage resources. As shown, the text 'amazonaws.com' allows for resolution to Amazon's various web services. Collectively, components 402, 404 and 406 form the host portion of the URL that identifies the type and geographic location of the online resource to be accessed.

Components 408 and 410 may form the path of the URL. The path may resolve to any suitable method or file for storing the electronic health information. For example, in the illustrated embodiment, the component 408 is structured in a way that indicates the region ('cloud-ca') where the electronic health information is being stored. It also contains an identifier ('5') for the institution that the electronic health information belongs to. Also, in the illustrated example, the electronic health information is patient-identifying information stored as a JavaScript Object Notation (JSON) file named 'patients.JSON' as indicated by the URL component 410. As will be understood by persons skilled in the art, JSON provides a simple way to exchange data that can be easily parsed. Example contents of a JSON file containing patient health information is discussed below in relation to FIG. 6.

Web service providers (e.g., Amazon AWS) traditionally provide endpoints for their web services in different geographical regions for the purpose of reducing data latency (e.g., to reduce the amount of time it takes to communicate with the web service from a given client device). In a traditional attempt to also comply with data residency requirements for electronic health information, one may attempt to address both latency requirements and data residency requirements at the same time. For example, such a solution may involve instantiating a server 130 and database 140 in every region where electronic health information is to be stored, so that both electronic health information and non-health information are stored regionally. However, as noted above, doing so may introduce technical and logistical complexities (e.g., related to data inconsistency across multiple regions for settings, maintenance of applications on multiple servers 130, and/or additional costs).

In the present embodiments, non-health information 144 is stored in a centralized manner in a single region, while the electronic health information is stored on a regionalized basis. While this may potentially increase data latency when accessing non-health information as compared to solutions where the non-health information is also regionalized, the present embodiments may help avoid the technical and logistical complexities that may come from regionalizing the server 130 and the database 140. At the same time, compliance with data residency requirements applicable to the electronic health information may be achieved.

Referring to FIG. 5, shown there generally as 500 is another example URL for accessing electronic health information, in accordance with at least one embodiment of the present invention. The URL 500 in FIG. 5 has components for regionalized access that is similar to what is shown in FIG. 4. However, whereas the URL in FIG. 4 was for storage of patient-identifying information, the URL is for storage of an ultrasound media file (e.g., an ultrasound image). For example, as shown, the component 502 of the URL 500 relates to a Joint Photographic Experts Group (JPEG) file. However, in other examples, the images may be stored in other file formats. Additionally or alternatively, the ultrasound media may be a cineloop or other movie file (e.g., stored as an Audio Video Interleave (AVI) file or the like video file format).

In FIG. 5, the example URL also contains a query string component 505. For example, the query string may include information that is used by the identified resource. As shown, the query string includes text related to authentication and/or encryption (e.g., security credentials) that allows a device to access the resource identified by the URL. While no query string is shown in the example URL of FIG. 4, in some embodiments, the URL may include a query string that includes search parameters (e.g., a Universally Unique Identifier (UUID)) for reading desired patient entries and/or for providing the patient-identifying information desired to be stored in the JSON file.

Referring back to FIG. 2, after the computing device 120 receives the second network location from the server 130 at act 214, at 218, the computing device 120 may use the second network location to store the electronic health information to the cloud object storage resource 150 identified by the second network location.

In the example embodiment shown in FIG. 2, the computing device 120 may perform an optional act to start a background process to store the electronic health information (act 216, as shown in dotted outline). In such embodiments, the computing device 120 may, at act 218, use the background process to access the second network location to store the electronic health information. In an embodiment where a background process is not used to upload electronic health information, act 218 may be performed using a foreground process.

In various embodiments, the electronic health information may include ultrasound media (e.g., images and/or cineloops) that have large file sizes. Depending on the available bandwidth and/or file size(s), uploading and storing such ultrasound media to the second network location may take time. This means that using a foreground process to perform the uploading and storing may require a user to keep the ultrasound application 122 in the foreground of the operating system while the uploading is performed. This may cause inconvenience for end users who desire to exit out of the ultrasound app 122 and/or switch to another application on the computing device 120 after they have begun an upload of exam data. Using a background process to upload the electronic health information may help address this inconvenience. However, using a background process to perform uploading may introduce certain challenges.

For example, in some embodiments, the operating system of the computing device 120 may place certain restrictions on the capabilities of a background process. E.g., in the iOS™ operating system, data transfers using a background process may not be performed using custom protocols, and are limited to being performed using Hypertext Transfer Protocol (HTTP) and/or HTTP Secure (HTTPS) protocols. Additionally or alternatively, background processes performing data uploads on the iOS™ operating system may be limited to upload tasks being performed from a file, such that uploads from data instances or a stream may fail after the ultrasound app 122 exits.

The present embodiments may be configured to operate within these constraints, so as to allow for uploading of electronic health information on operating systems of mobile computing devices 120.

For example, by using cloud object storage resources 150 to store the electronic health information, electronic health information may be accessed and uploaded to the second network location simply using HTTP or HTTPS protocols without need for use of a custom protocol. If other storage services were used (e.g., relational database storage), it may also have been necessary to instantiate computer processing resources in the geographic location where the data storage resource was instantiated, so as to communicate with the ultrasound app 120 using a custom protocol that receives the electronic health information and stores it into the data storage service. Storing electronic health information into cloud object storage resources 150 that are accessible via HTTP or HTTPS URLs may thus also allow for uploading of exam data using a background process.

In another example, the present embodiments may configure the electronic health information to be stored as a JSON file and/or as multimedia files (e.g., JPEG or AVI cineloop files). This also allows the embodiments to operate within another one of the restrictions noted above for uploading of data using a background process—the requirement that uploading be performed on a file. If patient-identifying information was stored in a database, it may not have been possible to use a background process to upload such information to the second network location because computer processing resources may again need to be instantiated in the same region where the data storage resource was instantiated to communicate with the computing device 120 using a custom protocol.

Referring back to FIG. 2, at 220, the electronic health information may be stored at the cloud object storage resource 150 at the second network location. Depending on the type of electronic health information being stored, the storage format may take different forms.

For example, referring to FIG. 6, shown there generally as 600 is an example of a file storing patient electronic health information, in accordance with at least one embodiment of the present invention. The example shown is a JSON file as was referred to above in the URL of FIG. 4. JSON files may contain attribute-value pairs and/or array data types used for storing data. As illustrated, the JSON file is formatted to store patient-identifying information, and each patient entry 602 is associated with a UUID 610.

Also, each patient entry 602 may be provided with a number of attributes-value pairs for a given patient. For example, as shown, there are attributes for "date_of_birth", "first_name", "middle_name", "last_name", and "gender". There are also attributes for "identifier" 612 to record an identifier for a given patient, and a "last_modified" attribute 616 to record a timestamp for when the patient entry 602 was last modified. Further, a patient entry 602 may include an "institution_id" attribute 614 to store an institution identifier that the patient may belong to. As illustrated, the JSON file only shows three patient entries 602, but as will be understood, in various implementations, the JSON patient file may contain numerous patient entries 602.

Storage of patient-identifying information in a JSON file is only one example format that can be used. In various embodiments, other formats for storing the data may also be used. In some embodiments, the patient-identifying information may be stored as unstructured data. In some embodiments, each patient entry may be stored in its own file or bit blob. In some embodiments, the patient-identifying information (regardless of what format it is stored in) may be encrypted.

In another example, if the electronic health information is ultrasound media, the media may be stored in various formats. When ultrasound image data is first generated, it may be provided in a data space (e.g., polar coordinate form). A scan conversion process can be performed to transform the image data from the data space to the display space (e.g., Cartesian coordinate form). Since the ultrasound media may potentially be displayed on displays with different characteristics, scan conversion may allow the same ultrasound image data to be adapted to the various sizes and/or resolutions of different displays.

In various embodiments, when performing act 220 of FIG. 2, electronic health information that is ultrasound media may be stored as pre-scan converted image data and/or post-scan converted image(s). For example, the computing device 120 may receive pre-scan converted ultrasound image data from an ultrasound scanner 110 (as shown in FIG. 1), and perform scan conversion to convert it to a suitable format for display on the computing device 120. In one example embodiment, the computing device 120 at act 218 of FIG. 2 can transmit the post-scan converted image(s) for storage at the cloud object storage resource 150. However, such post-scan converted image(s) may be best suitable for the particular display of the computing device 120 (which, e.g., may be a smart device such as a smartphone or a tablet computer), and may not scale/adapt suitably for other displays such as on the viewing device 160 (which, e.g., may be a desktop or laptop computer).

Thus, in additional or alternative embodiments, the computing device 120 may transmit pre-scan converted image data to the cloud object storage resource at act 218 for storage. In such embodiments, scan conversion may be performed when a viewing device 160 retrieves the ultrasound media for viewing.

In further embodiments, both pre-scan converted image data and post-scan converted image(s) may be stored at the cloud object storage resource 150. For example, in such embodiments, the post-scan converted image(s) may not be the image(s) from the computing device 120 that have been scan converted for the display thereon. Instead, the images may be scan converted to a generic 'web' resolution, for display at a viewing device 160. In various embodiments, this additional scan conversion may be performed by the computing device 120 and/or by the server 130. For example, if the server 130 is to perform this additional scan conversion, the server 130 may receive the pre-scan converted image data from the computing device 120 and/or it may read the pre-scan converted image data from a cloud object storage resource 150 after the computing device 120 has stored it thereon. This scan conversion act is not shown in FIG. 2.

Referring again back to FIG. 2, at 222, after the server 130 provides the second network location to the computing device 120, it may store an identifier of the electronic health information. The stored identifier may be usable by the server 130 to read the electronic health information from the second network location at a subsequent time. For example, this identifier may be a UUID associated with the ultrasound media and/or patient-identifying information being stored.

FIG. 2 showed only an example embodiment. Various modifications may be made. For example, the method 200 was generally described above as involving a computing device 120 storing electronic health information. However, in various embodiments, the acts discussed above as being performed by the computing device 120 may also be performed by the viewing device 160 (as shown in FIG. 1). For example, this may happen when a viewing device 160 views electronic health information (e.g., pursuant to the method of FIG. 3, discussed below), and edits such electronic health information for uploading to a cloud object storage resources 150. In various embodiments, the acts to store electronic health information indicated as being performed by the computing device 120 in FIG. 2 may be performed by the e-health storage module 164 provided on viewing device 160 (as shown in FIG. 1).

Also, the acts performed by the computing device 120 for receiving electronic health information 120 (act 202), retrieving a second network location (acts 204-214), and accessing the second network location to store the electronic health information (act 218) may not necessarily all be performed together in every instance, and not necessarily in the order shown. For example, in some embodiments, acts 204-214 to retrieve the second network location may be performed once (e.g., during selection or creation of an institution, or upon launching of the ultrasound app 122). Then, act 202 may be performed afterwards to receive electronic health information, and the computing device 120 may refer to the cached second network location to store electronic health information (act 218). While these embodiments are within the scope of the present disclosure, configuring the computing device 120 to perform requests for the second network location each time electronic health information is desired to be accessed may be desirable in certain instances.

For example, to provide enhanced security, the cloud object storage resource 150 may be locked when no access is expected. When electronic health information is expected to be stored or read, the cloud object storage resource 150 may be unlocked and a URL with authentication information and/or security credentials in the query string (such as is shown in FIG. 5) may be generated. This URL may time out after a period of time to ensure that even if the URL is re-used (e.g., by a nefarious third-party), no unauthorized access is permitted. Thus, in certain embodiments, the sending of a request for the second network location each time electronic health information is desired to be stored/read may serve a supplemental purpose of providing enhanced security (e.g., to indicate to the server 130 when the cloud object storage resource 150 is to be unlocked for accessed).

Figure 3:
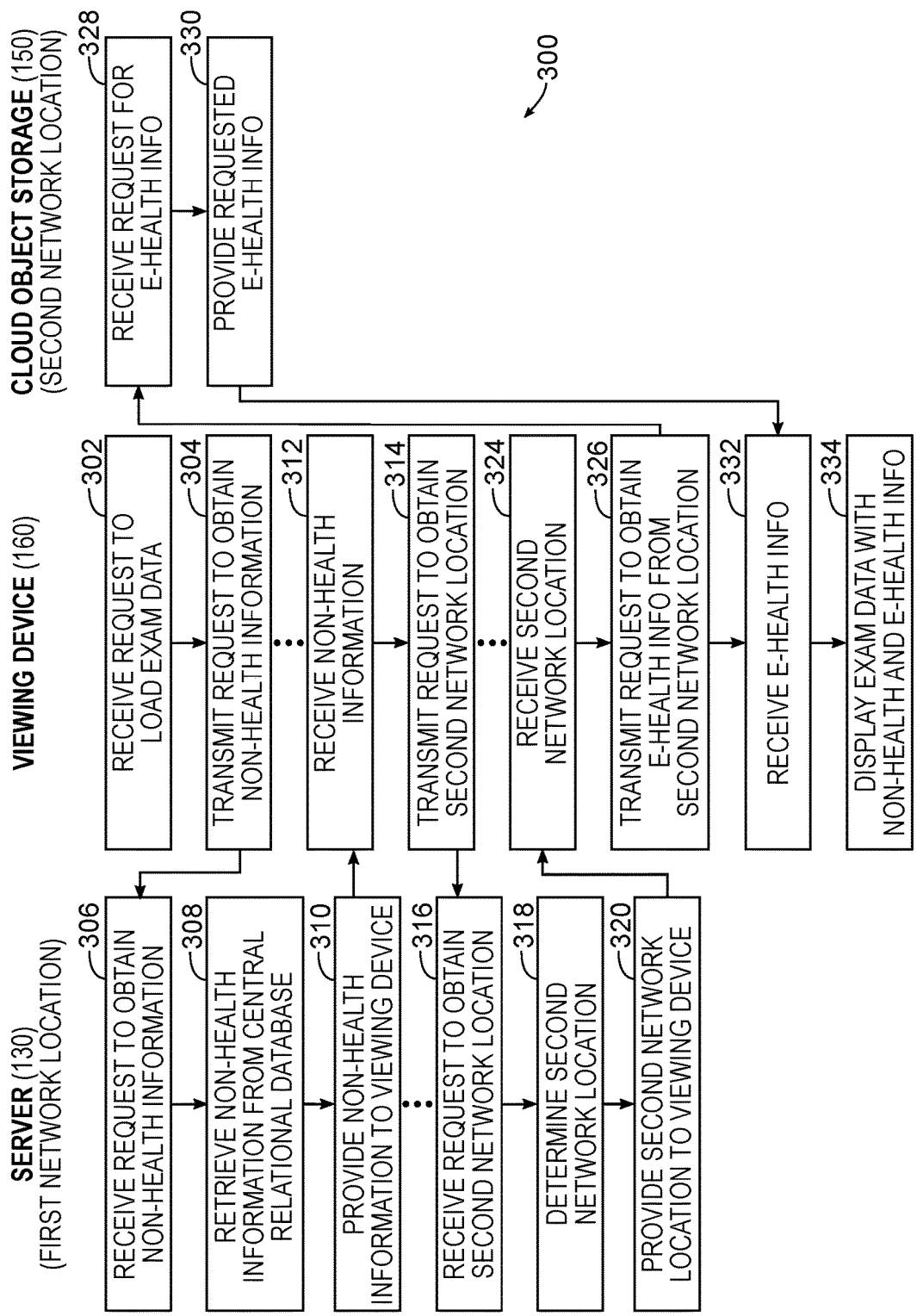
FIG. 3 is a flowchart diagram showing acts for reading electronic health information, in accordance with at least one embodiment of the present invention.

Referring to FIG. 3, shown there generally as 300 is a flowchart diagram showing acts for reading of electronic health information, in accordance with at least one embodiment of the present invention. The discussion above for FIG. 2 generally related to the storage of electronic health information from a computing device 120. However, the method of FIG. 3 relates generally to how stored electronic health information may be retrieved and accessed. In discussing the acts of FIG. 3, reference will also be made to various elements shown in FIG. 1 and the example user interface shown in FIG. 7. Method 300 generally illustrates interactions amongst the server 130, the viewing device 160, and a cloud object storage resource 150 shown in FIG. 1. In FIG. 3, various acts shown as being performed by the server 130 may be performed by the storage/locator service 132, and various acts shown as being performed by the viewing device 160 may be performed by the e-health reading module 166.

At 302, the viewing device 160 may receive a request to load exam data. For example, the browser 162 at the viewing device 160 may be able to load software (e.g., a web application and/or script) that can communicate with the server 130 to display exam data previously uploaded by the computing device 120. The web application may display a user interface that shows electronic health information (e.g., patient-identifying information and/or examination media), and other non-health information such as information identifying the institution and/or the medical practitioner performing the exam.

At 304, the viewing device 160 may transmit a request to obtain non-health information from the server 130 at the first network location. At 306, this request may be received at the server 130. At 308, the server 130 may retrieve the requested non-health information 144 from the central database 140 (as shown in FIG. 1). This information may be provided to the viewing device 160 (act 310), and received at the viewing device 160 (act 312). In various embodiments, the communications between the viewing device 160 and the server 130 described herein may be encrypted (e.g., using 128-bit Transport Layer Security (TLS) 1.2 encryption or higher).

As noted above, the non-health information may be stored in a database 140 whereas the electronic health information may be stored in cloud object storage resources 150. As discussed, storage of electronic health information in cloud object storage resources 150 may be desirable because they can be instantiated in different geographic regions without also instantiating cloud computing resources in those regions. Additionally or alternatively, storage of electronic health information using those resources may be accessed by a URL, such that it can be performed within the restrictions for background processes on certain operating systems of computing devices 120.

Since non-health information may not necessarily be subject to the same geographical storage (e.g., data residency) requirements as electronic health information, it may be stored in a centralized manner at the location of the server 130. Also, since non-health information is primarily being accessed by the server 130 that would not be subject to the restrictions for background processes on computing devices 120, a database 140 can be used for storage. Using a traditional database 140 to store non-health information may provide more flexibility to retrieve data in a structured manner (e.g., to run queries and the like) rather than simply storing the data using a cloud object storage resource 150.

Once the viewing device 160 has obtained the non-health information, it may proceed to obtain the electronic health information related to the exam data requested to be loaded at act 302.

At 314, the viewing device 160 may transmit a request to obtain a second network location for the electronic health information. This request may be received at the first network location where the server 130 is provided at act 316).

At 318, the server 130 may determine the second network location of the electronic health information (e.g. using the storage/locator service 132). Similar to the discussion above for storing electronic health information, the storage/locator service 132 may be able to determine the second network location based on an institution profile associated with a logged-in user at the viewing device 160. For example, the storage/locator service 132 may able to look up the second network location for the institution profile using the institution-based geographical region settings 142 stored in the regional database 140 (as shown in FIG. 1).

Additionally or alternatively, the determination of the second network location setting may determined be based on GPS or other geographic identifying information of the viewing device 160, as noted above. In some embodiments, such geolocation information may be used as an additional layer of security to confirm the geographical location of the second network location determined from the institution-based geographical region location setting. For example, if the geographical region setting of the institution profile indicates that a U.S.-based cloud object storage resource 150A is to be used, but the geolocation information from the viewing device 160 indicates that the geographical location of the viewing device 160 is outside of the U.S., then viewing access to the electronic health information may be denied.

At 320, the server 130 may provide the second network location to the viewing device 160. The viewing device 160 may then receive the second network location (act 324).

At 326, the viewing device 160 may transmit a request to obtain the electronic health information from the second network location. This request may be received at the cloud object storage resource 150 identified by the second network location (act 328). In various embodiments, the request may be accompanied by an identifier that allows for identification of the item of electronic health information at the cloud object storage resource 150. For example, this identifier may be a UUID that can identify an ultrasound media item associated with the exam requested at act 302 (e.g., as is shown in FIG. 5, incorporated into the file name of the URL component 502).

At 330, the cloud object storage resource 150 may provide the requested electronic health information to the viewing device 160. The electronic health information may then be received at the viewing device 160 (act 332). At 334, the viewing device 160 may display the requested examination data that has both non-health information and electronic health information.

As discussed above, if the electronic health information is ultrasound media, it may be stored in in a pre-scan converted format and/or a post-scan converted format at the cloud object storage resource 150. For example, if only the pre-scan converted image data is available, the viewing device 160 may perform scan conversion prior to displaying the ultrasound image data at act 334. In various embodiments, the viewing device 160 may provide the pre-scan converted data to the server 130 for performing scan conversion. If the post-scan converted image(s) is/are available (e.g., if scan conversion to a generic 'web' format has already been performed upon storage), then the viewing device may retrieve the post-scan converted image directly (e.g., via a URL) and simply render it.

Storing only the pre-scan converted image data on the cloud object storage resource 150 may save storage space at the cloud object storage resource 150. However, doing so may reduce performance when ultrasound media is retrieved because scan conversion may need to be performed dynamically upon a request for reading the ultrasound media. In contrast, performing the scan conversion in advance and storing the post-scan converted image data at the cloud object storage resource 150 may allow for improved performance when ultrasound media is selected to be viewed.

In a further embodiment, it may be possible to store the pre-scan converted ultrasound image data on the cloud object storage resource 150 (e.g., at act 220 of FIG. 2), and perform scan conversion on an on-demand basis when a request to read and view the ultrasound media item is requested. Upon request, scan conversion to the generic 'web' format can be performed. Once scan conversion is performed, the post-scan converted ultrasound image can be stored on the cloud object storage resource 150 for future reuse. Configuring the storage of the ultrasound media in this manner may achieve a balance of the competing interests for reduced storage and increased performance. E.g., storage space will generally be reduced for ultrasound media that may never be accessed from the viewing device 160. However, once a read request is made, scan conversion can be performed so that subsequent reading of the same ultrasound media may be performed with minimal performance lag.

Figure 7:
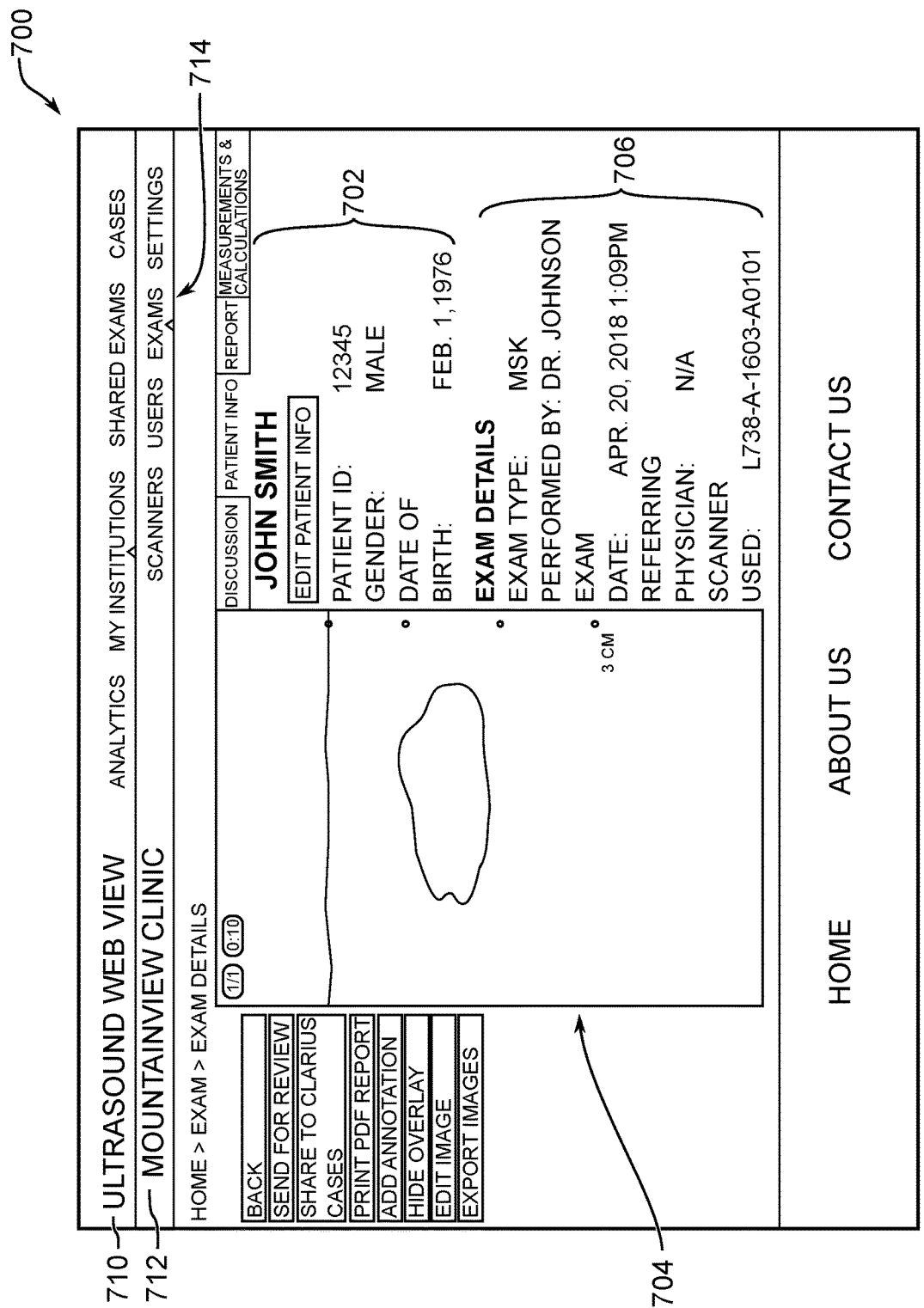
FIG. 7 is an example screenshot of a user interface that displays non-health information read from a first network location and electronic health information read from a second network location, in accordance with at least one embodiment of the present invention.

Referring to FIG. 7, shown there generally as 700 is an example screenshot of a user interface that displays non-health information read from a first network location and electronic health information read from a second network location, in accordance with at least one embodiment of the present invention. For example, the user interface may be displayed on a browser 162 of the viewing device 160 (as shown in FIG. 1). In the illustrated example, the user interface may be part of an "Ultrasound Web View" 710 web application accessible from the server 130, where a user may log in and access software features for their institution "Mountainview Clinic" 712. One example feature 714 available on this web application may be to view examinations they acquired using ultrasound scanner 110 and computing device 120 (as shown in FIG. 1), and stored using the method of FIG. 2.

To view the exam data, the browser 162 at a viewing device 160 may be configured to perform the method of FIG. 3 to read both non-health information from server 130 and electronic health information specific to a patient from a geographic region-specific cloud object storage resource 150. This may result in a view of exam details as shown in FIG. 7 where patient-identifying information 702 can be viewed with an associated ultrasound media item 704 (e.g., a cineloop with depth indications and a structure viewable). The example user interface may also display the non-health information 706 such as metadata associated with the examination. For example, such metadata may include exam type (e.g., Musculoskeletal or "MSK"), the medical professional performing the examination (e.g., "Dr. Johnson"), date of the examination, and an identifier for an ultrasound scanner 110 used to perform the examination (e.g., "L7380-A-1603-A0101").

Notably, non-health information 706 and patient-identifying information 702 may be viewed together in the same user interface at the viewing device 160. This is despite the non-health information being obtained from a first network location, and the electronic health information (e.g., the patient-identifying information 702) being obtained from the second network location.

In the embodiments discussed above in relation to FIGS. 2 and 3, reading and/or writing of electronic health information to the cloud object storage resources 150 have generally been performed by the computing device 120 or the viewing device 160 directly, after obtaining the second network location from the server 130. However, in alternate embodiments, certain electronic health information may be accessed through server 130, with the server 130 performing the direct communication with the second network location to read/write the desired electronic health information.

For example, as discussed above, an example format in which patient-identifying information may be stored is the JSON format (such as was illustrated in FIG. 6). Since this file can be stored on a cloud object storage resource 150 that may not have a corresponding computer processing resource instantiated in that same geographic location, any processing of this file (e.g., reading or writing of specific patient entries) may have to be performed at the device directly communicating with the cloud object storage resource 150. This may result in the computing device 120 and/or the viewing device 160 reading the entire JSON file so that it can be parsed thereon (e.g., for identifying the desired patient entry, and/or appended to when adding a patient entry).

To prevent a potentially-large JSON file from being transferred to and from the computing device 120 and/or viewing device 160, in some embodiments, the reading and writing of the JSON file may be performed by the server 130. For example, in such embodiments, the storage/locator service 132 (as shown in FIG. 1) may be configured to also provide API calls that allow for reading, editing and/or writing patient entries into a JSON file stored in a geographically-regionalized cloud object storage resource 150.

For example, when the ultrasound app 122 at the computing device 120 and/or the e-health storage module 164 on the viewing device 160 stores patient entries, it may communicate with the server 130 to request that the storage/locator service 132 write to the JSON file in the suitable cloud object storage resource 150. The determination of the suitable cloud object storage resource 150 may be performed in a manner similar to what which was described above.

Similarly, when the e-health reading module 166 reads patient entries, it may additionally or alternatively communicate with server 130 to request that the storage/locator service 132 process the JSON file from the suitable cloud object storage resource 150 and read the desired patient entry. In some embodiments, the e-health reading module 166 at viewing device 160 may communicate directly with the cloud object storage resource 150 at the second network location for one type of electronic health information; and indirectly with the cloud object storage resource 150 at the second network location (through server 130 at the first network location) for another type of electronic health information. For example, there may be direct communication for ultrasound media files (e.g., ultrasound images and cineloops), and indirect communication for patient-identifying information (such as patient entries stored in a JSON file which may first need to be processed by the server 130). This is so even though both types of electronic health information are ultimately stored on a geographically-regionalized cloud object storage resources 150 at the second network location. In these embodiments, after the different types of electronic health information is retrieved, a uniform user interface for viewing exams such as was shown in FIG. 7 may generated for viewing at the browser 162.

In a further embodiment, the e-health reading module 166 at viewing device 160 may not communicate directly with the cloud object storage resources 150 at all. For example, in these embodiments, the retrieval of all types of electronic health information (e.g., ultrasound media, patient-identifying information) from the appropriate cloud object storage resource 150 may be performed indirectly through the server 130. For example, in some embodiments, the storage/locator service 132 may be configured to provide additional APIs for this functionality.

Additionally or alternatively, the e-health reading module 166 shown in FIG. 1 as provided on the browser 162 in FIG. 1 may instead be provided on the server 130. This may allow the browser 162 to simply request the display of exam data from the server 130 while the server 130 manages the retrieving of the electronic health information from the geographic location-appropriate cloud object storage resource 150 (and without the viewing device 160 directly retrieving the electronic health information from a cloud object storage resource 150). This may allow the server 130 to generate a uniform user interface (such as is shown in FIG. 7), and offload some of the processing burden of generating the user interface from the viewing device 160 to the server 130.

In a further embodiment, the e-health storage modules 124, 164 may not communicate directly with the cloud object storage resources 150 either. For example, in these embodiments, the storage of all types of electronic health information (e.g., ultrasound media, patient-identifying information) onto the appropriate cloud object storage resource 150 may be performed indirectly through the server 130. For example, the storage/locator service 132 may provide software functionality for accomplishing this. In such embodiments, the ultrasound app 122 on the computing device 120 may transmit non-health information and electronic health information to the server 130, and the server 130 may then forward the electronic health information to the appropriate geographic location-specific cloud object storage resource 150 for storage.

Figure 8A:
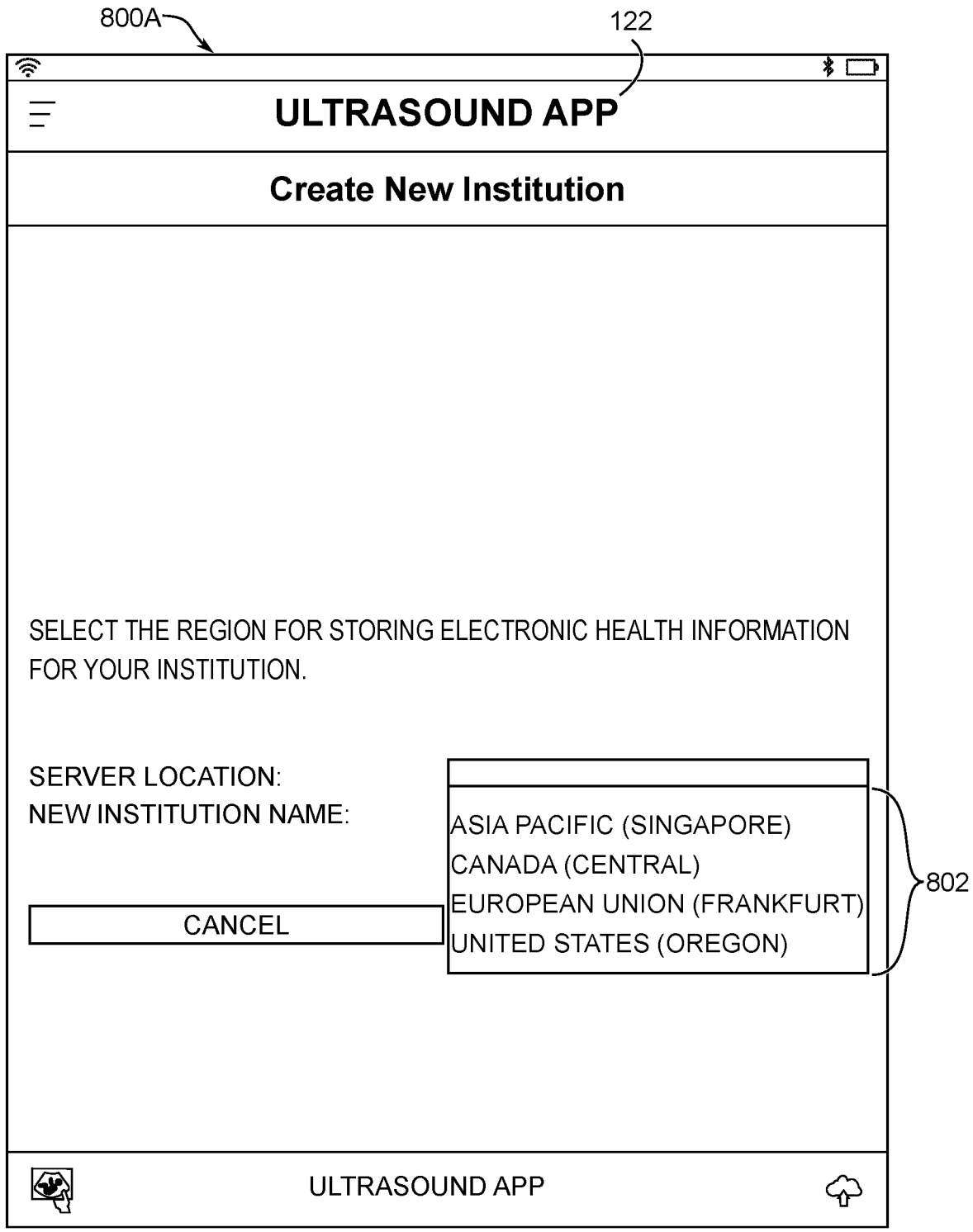
FIGS. 8A and 8B show example screenshots of a user interface on a computing device for selecting a geographical region storage setting, in accordance with at least one embodiment of the present invention.
Figure 8B:
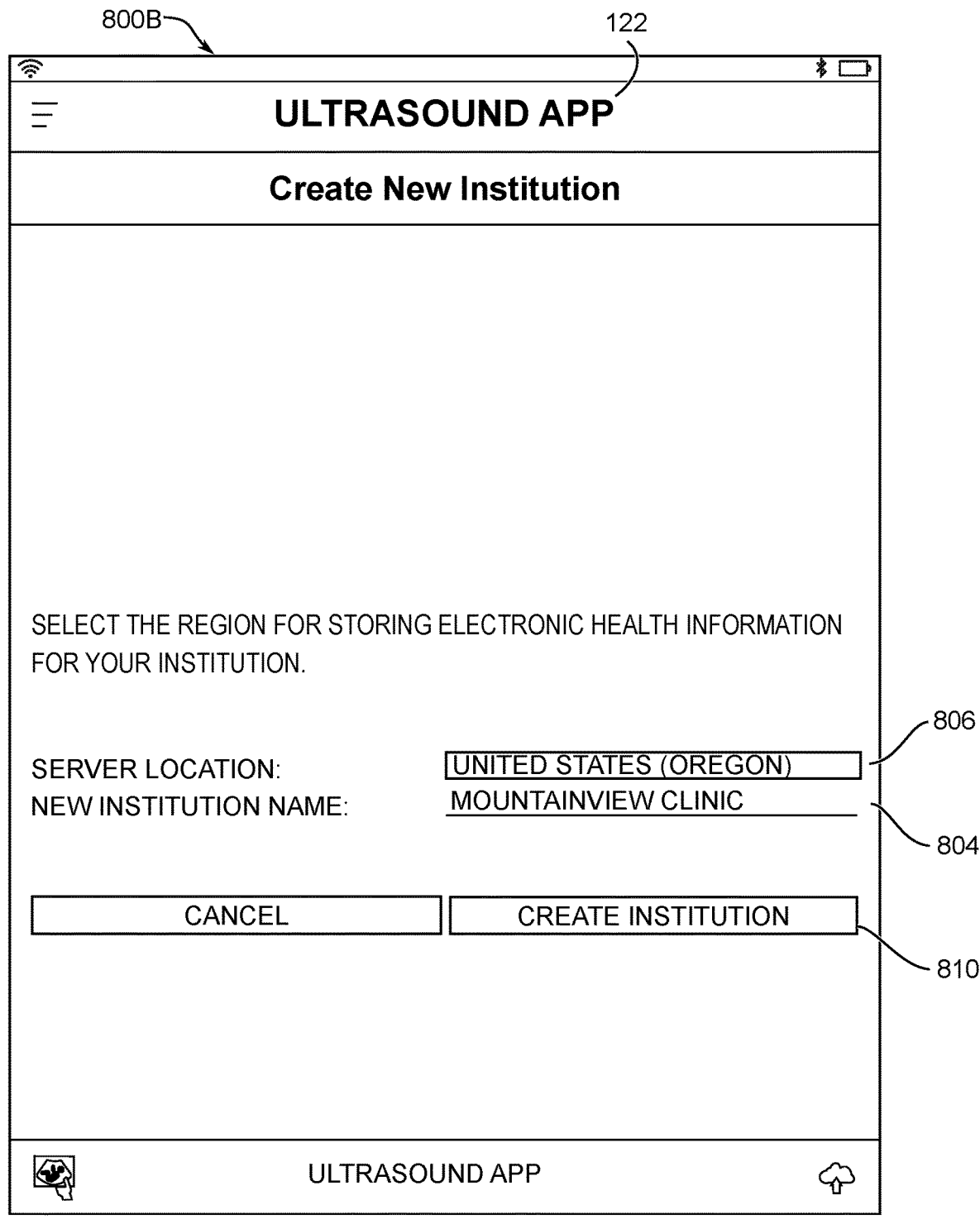

Referring to FIGS. 8A and 8B shown there generally as 800A and 800B are example screenshots of a user interface on a computing device 120 for selecting a geographical region storage setting, in accordance with at least one embodiment of the present invention. The discussion above has generally related to the storage of electronic health information (FIG. 2), and the reading of stored electronic health information (FIG. 3). In certain embodiments discussed above, the determination of the second network location from which to store and retrieve electronic health information was based on an institution profile setting. FIGS. 8A and 8B show example screenshots for how that setting may first be set.

In an example embodiment, this setting may first be set upon the creation of a new institution. For example, the user interfaces of FIGS. 8A and 8B may be shown by the ultrasound app 122 when a user activates an ultrasound scanner 110 for the first time and is prompted to create an institution with which to be associated. FIG. 8A shows an example screenshot of the ultrasound app 122 that prompts a user to select a region for storing electronic health information for a newly-created institution. As illustrated, the user interface presents a combo box 802 for selecting from four available geographic regions: "Asia Pacific (Singapore)", "Canada (Central)", "European Union (Frankfurt)", and "United States (Oregon)". As discussed above, these regions reflect the available second network locations where cloud object storage resources 150 have been instantiated and can be accessed (e.g., written into and read from). In the illustrated example, four geographic regions are available for selection. However, in various embodiments, additional or fewer institutions may be available. Moreover, new regional storage locations may be made available for selection as they are instantiated.

Upon selection of one of these options, the user interface of the ultrasound app 122 may proceed to display that which is shown in FIG. 8B. FIG. 8B shows an example screenshot 800B where the "United States (Oregon)" option 806 has been selected. With the combo box user interface control 802 of FIG. 8A closed, another user interface control (e.g., a text field 804) for entering the name of the institution may be displayed. In the illustrated example, "Mountainview Clinic" has been entered. Once the geographic region 806 and the institution name 804 has been entered, the "Create Institution" button 810 may be selected to create the institution.

While a number of exemplary aspects and embodiments have been discussed above, those of skill in the art will recognize that may be certain modifications, permutations, additions and sub-combinations thereof. While the above description contains many details of example embodiments, these should not be construed as essential limitations on the scope of any embodiment. Many other ramifications and variations are possible within the teachings of the various embodiments.

Interpretation of Terms

Unless the context clearly requires otherwise, throughout the description and the claims:
 "comprise", "comprising", and the like are to be construed in an inclusive sense, as opposed to an exclusive or exhaustive sense; that is to say, in the sense of "including, but not limited to";
 "connected", "coupled", or any variant thereof, means any connection or coupling, either direct or indirect, between two or more elements; the coupling or connection between the elements can be physical, logical, or a combination thereof;
 "herein", "above", "below", and words of similar import, when used to describe this specification, shall refer to this specification as a whole, and not to any particular portions of this specification;
 "or", in reference to a list of two or more items, covers all of the following interpretations of the word: any of the items in the list, all of the items in the list, and any combination of the items in the list;
 the singular forms "a", "an", and "the" also include the meaning of any appropriate plural forms.

Unless the context clearly requires otherwise, throughout the description and the claims:
 Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

For example, while processes or blocks are presented in a given order herein, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The invention may also be provided in the form of a program product. The program product may comprise any non-transitory medium which carries a set of computer-readable instructions which, when executed by a data processor (e.g., in a controller and/or ultrasound processor in an ultrasound machine), cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or pre-programmed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples but should be given the broadest interpretation consistent with the description as a whole.

What is claimed is:
1. A method for storage of ultrasound examination data, the method performed by a server at a first network location, the method comprising:
 receiving a request from an application on a computing device in communication with an ultrasound scanner, the computing device configured to store data associ- ated with an ultrasound examination acquired using the ultrasound scanner, the data comprising patient information associated with the ultrasound examination and non-health information associated with the ultrasound examination, wherein the request is for a second network location that is usable by the computing device to store the patient information associated with the ultrasound examination, and the second network location is different from the first network location;

determining the second network location for storing the patient information associated with the ultrasound examination;

providing the second network location to the computing device, wherein when storing the data associated with the ultrasound examination, the application at the computing device: stores the non-health information associated with the ultrasound examination at the server at the first network location, and stores patient information associated with the ultrasound examination at the second network location, and providing different network locations for different geographical region storage settings, wherein the server at the first network location is configured to store non-health information associated with other ultrasound examinations, which have geographical region storage settings different from a geographical region storage setting for the ultrasound examination, centrally at the first network location.

2. The method of claim 1, wherein when determining the second network location, the method further comprises:
looking up the geographical region storage setting for the ultrasound examination, and
selecting the second network location based on the geographical region storage setting.

3. The method of claim 2, wherein the geographical region storage setting is associated with an institution profile of a logged-in user at the computing device.

4. The method of claim 1, further comprising:
storing an identifier of the patient information associated with the ultrasound examination, and the identifier is usable by the server to read the patient information associated with the ultrasound examination from the second network location.

5. The method of claim 1, further comprising:
providing a location service that, when accessed, returns a network location address corresponding to the second network location provided to the computing device, the network location address being usable by the server to read the patient information associated with the ultrasound examination.

6. A method for storage of ultrasound examination data acquired from an ultrasound scanner, the method performed by an application executing on a computing device in communication with the ultrasound scanner, the method comprising:
identifying data associated with an ultrasound examination acquired from the ultrasound scanner, the data comprising patient information associated with the ultrasound examination and non-health information associated with the ultrasound examination;
transmitting a request to a server at a first network location, the request for retrieving a second network location that is usable by the computing device to store the patient information associated with the ultrasound examination, the second network location being different from the first network location, wherein the server:
determines the second network location for storing the patient information associated with the ultrasound examination,
provides the second network location to the computing device; and
provides different network locations for different geographical region storage settings, wherein the server at the first location is configured to store non-health information associated with other ultrasound examinations, which have geographical region storage settings different from a geographical region storage setting for the ultrasound examination, centrally at the first network location;
receiving the second network location from the server; and
to store the data associated with the ultrasound examination, storing: the non-health information associated with the ultrasound examination at the server at the first network location, and the patient information associated with the ultrasound examination at the second network location.

7. The method of claim 6, wherein the second network location resolves to a data storage service accessible by the computing device via a Uniform Resource Identifier (URI), and the storing of the patient information associated with the ultrasound examination at the second network location is performed via the URI.

8. A system for storage of ultrasound examination data, the system comprising:
an ultrasound scanner;
a computing device for communicating with the ultrasound scanner and for executing an application for receiving data associated with an ultrasound examination acquired using the ultrasound scanner, wherein the data comprises patient information associated with the ultrasound examination and non-health information associated with the ultrasound examination; and
a server for communicating with the computing device, the server being at a first network location, and accessible by the computing device to store the non-health information associated with the ultrasound examination, and the server being configured to:
receive a request from the computing device for a second network location, the second network location usable for storing the patient information associated with the ultrasound examination at the second network location, the second network location being different from the first network location,
determine the second network location for storing the patient information associated with the ultrasound examination, and
provide the second network location to the computing device;
wherein when storing the data associated with the ultrasound examination, the application at the computing device: stores the non-health information associated with the ultrasound examination at the server at the first network location, and stores patient information associated with the ultrasound examination at the second network location; and
wherein the server provides different network locations for different geographical region storage settings, and the server at the first location is further configured to store non-health information associated with other ultrasound examinations, which have geographical region storage settings different from a geographical region storage setting for the ultrasound examination, centrally at the first network location.

9. The system of claim 8, wherein when determining the second network location, the server is further configured to:
   look up the geographical region storage setting for the ultrasound examination, and
   select the second network location based on the geographical region storage setting.

10. The system of claim 9, wherein the geographical region storage setting is associated with an institution profile of a logged-in user at the computing device.

11. The system of claim 8, wherein the server is further configured to store an identifier of the patient information associated with the ultrasound examination, and the identifier is usable by the server to read the patient information associated with the ultrasound examination from the second network location.

12. The system of claim 8, wherein the server is further configured to provide a location service that, when accessed, returns a network location address corresponding to the second network location provided to the computing device, the network location address being usable by the server to read the patient information associated with the ultrasound examination.

13. The system of claim 8, wherein the second network location resolves to a data storage service accessible by the computing device via a Uniform Resource Identifier (URI).

14. The system of claim 13, wherein the server executes at least one process at the first network location to store the non-health information associated with the ultrasound examination in a database at the first network location.

* * * * *